(12) United States Patent
Boulanger (10) Patent No.: US 12,329,912 B2
(45) Date of Patent: Jun. 17, 2025

(54) INSTALLATION FOR SUPPLYING THERAPEUTIC GAS TO A PATIENT WHILE TAKING ACCOUNT OF THE LOSSES OF LEAKTIGHTNESS AT THE MASK

(71) Applicant: L'Air Liquide, Société Anonyme pour l'Etude et l'Exploitation des Procédés Georges Claude, Paris (FR)

(72) Inventor: Thierry Boulanger, Philadelphia, PA (US)

(73) Assignee: L'Air Liquide, Société Anonyme pour l'Etude et l'Exploitation des Procédés Georges Claude, Paris (FR)

(*) Notice: Subject to any disclaimer, the term of this patent is extended or adjusted under 35 U.S.C. 154(b) by 757 days.

(21) Appl. No.: 17/570,639

(22) Filed: Jan. 7, 2022

(65) Prior Publication Data

US 2022/0211970 A1    Jul. 7, 2022

(30) Foreign Application Priority Data

Jan. 7, 2021 (FR) ...................................... 2100102

(51) Int. Cl.
*A61M 16/20* (2006.01)
*A61M 16/00* (2006.01)
(Continued)

(52) U.S. Cl.
CPC ...... *A61M 16/203* (2014.02); *A61M 16/0003* (2014.02); *A61M 16/0051* (2013.01);
(Continued)

(58) Field of Classification Search
CPC .... A61M 16/00–0003; A61M 16/0009; A61M 16/0051; A61M 16/0075–0084;
(Continued)

(56) References Cited

U.S. PATENT DOCUMENTS

| 2004/0016433 A1* | 1/2004 | Estes ................. | A61M 16/0069 128/204.21 |
| 2015/0107593 A1* | 4/2015 | Truschel ........... | A61M 16/0069 128/204.22 |

(Continued)

FOREIGN PATENT DOCUMENTS

| CN | 105771049 | 6/2016 |
| EP | 3 701 992 | 9/2020 |
| WO | WO 99 61090 | 12/1999 |

OTHER PUBLICATIONS

French Search Report for corresponding 2100102, Sep. 21, 2021.

*Primary Examiner* — Rachel T Sippel
(74) *Attorney, Agent, or Firm* — Allen E. White (57) ABSTRACT

The invention relates to an installation (40) for supplying therapeutic gas, comprising a source (3) of therapeutic gas, a gas delivery apparatus (1) and a respiratory interface (10). The gas delivery apparatus (1) comprises a deformable reservoir fed with gas, a control unit with microprocessor which controls a valve device for controlling the flow rate of gas, a pressure sensor configured to perform gas pressure measurements at the respiratory interface (10) and to supply the gas pressure measurements to the control unit, a flow rate sensor to measure the flow rate of gas supplied and to supply the gas flow rate measurements to the control unit, and alarm means. The control unit is configured to estimate the leaks at the respiratory interface on the basis of the measurements of pressure and of flow rate, in order to ensure a correct concentration of the therapeutic gas in the respiratory interface.

15 Claims, 2 Drawing Sheets

(51) Int. Cl.
*A61M 16/06* (2006.01)
*A61M 16/12* (2006.01)

(52) U.S. Cl.
CPC .......... *A61M 16/06* (2013.01); *A61M 16/122* (2014.02); *A61M 2016/0027* (2013.01); *A61M 2016/0036* (2013.01); *A61M 2205/15* (2013.01); *A61M 2205/581* (2013.01); *A61M 2205/583* (2013.01)

(58) Field of Classification Search
CPC .. A61M 16/021–024; A61M 16/06–08; A61M 16/0841–0883; A61M 16/10–1005; A61M 16/12–125; A61M 16/20–209; A61M 2016/0015–0042; A61M 2016/102; A61M 2205/15; A61M 2205/18; A61M 2205/581; A61M 2205/583
See application file for complete search history.

(56) References Cited

U.S. PATENT DOCUMENTS

| | | | | |
|---|---|---|---|---|
| 2021/0338950 A1* | 11/2021 | Peter | .................... | A61M 16/104 |
| 2023/0116240 A1* | 4/2023 | Payton | ................. | A61B 5/7228 |
| | | | | 128/204.23 |

* cited by examiner

INSTALLATION FOR SUPPLYING THERAPEUTIC GAS TO A PATIENT WHILE TAKING ACCOUNT OF THE LOSSES OF LEAKTIGHTNESS AT THE MASK

CROSS REFERENCE TO RELATED APPLICATIONS

This application claims the benefit of priority under 35 U.S.C. § 119 (a) and (b) to French Patent Application No. 2100102, filed Jan. 7, 2021, the entire contents of which are incorporated herein by reference.

BACKGROUND

The invention relates to an installation for supplying therapeutic gas, comprising a gas delivery apparatus and a breathing mask with an outlet port for exhaled gas, serving to supply a therapeutic gas (i.e. pure gas or a gas mixture) to a patient while taking account of the possible leaks at the respiratory interface, such as a face mask, that is to say any loss of leaktightness on the perimeter of the respiratory interface, and possible dilution of the therapeutic gas by ambient air entering the mask on account of said leaks.

Certain therapies require that therapeutic gas made up of a mixture of several gaseous constituents be administered to conscious patients. It is thus known to use an equimolar mixture (50%/50%) of nitrous oxide ($N_2O$) and oxygen ($O_2$) in order to reduce anxiety, produce a sedative effect and/or attenuate acute pain. Likewise, it has been proposed to use a mixture of argon and oxygen (60 vol % Ar/40 vol % $O_2$), inhaled before and during, or even after, a mechanical thrombectomy procedure, in order to treat cerebrovascular accidents (CVA).

The inhalation of the therapeutic gas (i.e. one or more constituents) by a patient is generally effected continuously or intermittently via a breathing mask, typically a face mask, i.e. a mask covering the nose and mouth.

During continuous administration, a continuous flow rate of gas, exceeding the minute ventilation of the patient (i.e. the mean volume of gas inhaled by the patient in one minute), is delivered continuously during the inspiratory and expiratory phases of the patient. During the inspiratory phases, the patient inhales the gas contained in a deformable reservoir, whereas, during the expiratory phases, the gas fills the deformable reservoir again in order to prepare for the following inspiratory phase.

However, the administration of the gas encounters a problem during the treatment of certain pathologies, for example during a mechanical thrombectomy in the treatment of CVA. In fact, on account of the space constraints arising in the treatment of these pathologies, the gas delivery apparatus generally has to be placed quite far from the patient's head in the operating theatre or the like and fluidically connected to the mask, distributing the gas to said patient, via one or more gas supply tubes, that is to say one or more flexible hoses measuring several metres in length, typically about 3 or 4 metres, or more.

However, on account of their length, these gas supply tubes generate additional resistance to inhalation, that is to say the patient has to produce a negative pressure (i.e. a vacuum) in order to be able to inhale gas and meet their respiratory needs, all the more so as the resistance of the tubes increases.

In the event of "leaks" at the level of the mask, that is to say losses of fluidic leaktightness at the perimeter of the mask in contact with the patient's face, this negative pressure entrains ambient air, which then enters the mask and dilutes the inhaled gas, during the inspiratory phases of the patient.

This undesired dilution of the therapeutic gas by ambient air is highly problematic, as it may lead to a significant reduction in efficacy of the medical gas, i.e. of the therapeutic gas, administered to the patient. For example, the therapeutic properties of argon diminish once its concentration drops below 50% by volume.

This is medically unacceptable, and it is therefore necessary to ensure that the dilution of the therapeutic gas is not excessive, at the risk of not obtaining the expected clinical benefit, that is to say of not treating the patient effectively.

However, since the losses of leaktightness at the perimeter of the mask in contact with the patient's face are not constant, but extremely variable from one patient to another, in particular because of differences in anatomical morphology, the presence or absence of a beard, and so on, it is not possible to know in advance if the dilution of the therapeutic gas by the ambient air will generate a slight dilution or on the contrary an excessive dilution of the therapeutic gas in a given patient.

EP-A-3701992 proposes a gas delivery apparatus comprising a gas passage, a flexible reservoir and a processor unit. A differential pressure sensor serves to measure the pressure in the reservoir. A proportional valve permits adjustment of the flow rate in the gas passage according to the pressure measurements performed by the differential pressure sensor. The question of the leaks at the mask and of the resulting dilution of the therapeutic gas is not discussed.

In this context, the problem is to make available an installation for supplying therapeutic gas, i.e. pure gas or a gas mixture, to a patient, comprising a gas source, a gas delivery apparatus feeding a breathing mask with therapeutic gas coming from the gas source, in which the leaks at the mask are evaluated and taken into account so as to be able to guarantee that the therapeutic gas inhaled by the patient is at a sufficient concentration, that is to say an effective concentration, even in the event of undesired dilution by ambient air entering the mask via losses of leaktightness, i.e. leaks at the mask, and, if appropriate, to warn the user in the event of excessive dilution leading to a non-effective concentration of the therapeutic gas.

SUMMARY

A solution according to the invention therefore relates to an installation for supplying therapeutic gas to a patient, comprising:
- a source of gas comprising at least one therapeutically active compound at a given initial concentration ($C_{ini}$),
- a gas delivery apparatus fed with gas by said gas source, and
- a respiratory interface provided with at least one exhalation port which is fed with gas by said gas delivery apparatus, and in which the gas delivery apparatus comprises:
- an internal gas passage in fluidic communication with a deformable reservoir in order to feed the deformable reservoir with gas,
- a valve device arranged on the internal gas passage, upstream of the deformable reservoir, in order to control the flow rate of gas circulating in the internal gas passage,
- a control unit with microprocessor which controls the valve device in order to control the flow rate of gas passing through the valve device and feeding the deformable reservoir with gas, a pressure sensor configured to perform one or more gas pressure measurements ($P_{mask}$) at the respiratory interface and to supply said gas pressure measurement(s) ($P_{mask}$) to the control unit, a flow rate sensor arranged in the internal gas passage in order to measure the flow rate of supplied gas ($Q_{alim}$) circulating in said internal gas passage and to supply said gas flow rate measurement(s) (Q) to the control unit, and alarm means, in particular an acoustic and/or visual alarm.

Moreover, the gas delivery apparatus of the installation according to the invention for supplying therapeutic gas additionally comprises storage means for storing a concentration threshold value ($C_{min}$) of therapeutically active compound, and the control unit is configured to:

determine the exhaled flow rate ($Q_{exp}$) escaping through the exhalation port of the respiratory interface on the basis of the gas pressure ($P_{mask}$) measured at the respiratory interface, during at least one expiratory phase of said patient, determine, on the basis of the flow rate of supplied gas ($Q_{alim}$) during an inspiratory phase of the patient and of the exhaled flow rate ($Q_{exp}$) during the expiratory phase following said inspiratory phase of the patient, volumes of gas supplied ($V_{alim}$) and exhaled ($V_{exp}$), determine, on the basis of the volumes of gas supplied ($V_{alim}$) and exhaled ($V_{exp}$), from the integral of the gas pressure ($P_{mask}$) during the inspiratory phase and the integral of the gas pressure ($P_{mask}$) during the expiratory phase, at least one leakage volume ($V_{leak}$) entering the respiratory interface during said inspiratory phase, determine, on the basis of the leakage volume ($V_{leak}$) and of the volumes of gas supplied ($V_{alim}$) and exhaled ($V_{exp}$), a rate of dilution of the gas, calculate the actual concentration ($C_{actual}$) of said at least one therapeutically active compound in the respiratory interface on the basis of the initial concentration ($C_{ini}$) of said at least one therapeutically active compound and of the determined rate of dilution of the gas, compare the calculated actual concentration ($C_{actual}$) to the concentration threshold value ($C_{min}$) of therapeutically active compound, stored by the storage means, and order the alarm means to trigger an acoustic and/or visual alarm when the calculated actual concentration ($C_{actual}$) is below said stored concentration threshold value ($C_{min}$) of therapeutically active compound.

In the context of the invention:

the term "pressure" is used to generally denote a positive pressure (>0 bar), zero pressure (=0 bar) or negative pressure (<0 bar), that is to say a vacuum.

the pressures are expressed in bar or mbar relative.

the "−" sign before a pressure value denotes that the pressure is negative, that is to say that it is a vacuum (i.e. below atmospheric pressure).

the "+" sign before a pressure value denotes that the pressure is positive (i.e. above atmospheric pressure).

the term "therapeutic gas" denotes a gas with one or more gaseous constituents or compounds, that is to say a "pure" gas or a gas mixture, of which at least one compound or constituent is therapeutically active and/or effective.

in "control unit", the term "unit" is equivalent to the terms "devices", "apparatuses", "means", "system" or similar, and the term "control" is equivalent to the terms "command, "pilot", "process" or similar.

Depending on the embodiment in question, the installation of the invention can comprise one or more of the following features:

the gas source comprises argon as therapeutically active compound at an initial concentration ($C_{ini}$) of greater than 50% by volume, preferably an argon/oxygen mixture.

the argon/oxygen mixture contains 35 to 45 vol % $O_2$ and 55 to 65 vol % Ar, preferably a mixture containing 38 to 43 vol % $O_2$ and 57 to 62 vol % Ar, in particular a mixture made up of 40 vol % $O_2$ and 60 vol % Ar.

the initial concentration ($C_{ini}$) is stored, for example by a microprocessor of the control unit or by a storage memory.

the initial concentration ($C_{ini}$) can be fixed, that is to say indicated or entered in the apparatus, via a human-machine interface or HMI.

the concentration threshold value ($C_{min}$) stored is equal to 50% by volume.

the concentration threshold value ($C_{min}$) is stored by the storage means.

the storage means comprise a flash memory.

the control unit of the gas delivery apparatus is configured to determine the exhaled flow rate ($Q_{exp}$) on the basis of the gas pressure ($P_{mask}$) measured at the respiratory interface and of at least one stored conversion table.

when the control unit determines that the gas pressure ($P_{mask}$) measured in the respiratory interface is less than or equal to a given pressure threshold value ($P_{threshold}$), i.e. $P_{mask} \leq P_{threshold}$, said control unit is configured to control the valve device to increase the flow rate of therapeutic gas passing through said valve device and feeding the deformable reservoir.

the pressure threshold value ($P_{threshold}$) is less than or equal to 0 mbar.

the pressure threshold value ($P_{threshold}$) is less than or equal to −0.25 mbar, preferably less than or equal to −0.5 mbar.

the pressure threshold value ($P_{threshold}$) is stored in the control unit.

the pressure threshold value ($P_{threshold}$) is stored by the microprocessor or by a data storage memory.

the pressure threshold value ($P_{threshold}$) is adjustable.

the internal gas passage comprises one or more ducts, pipes or similar.

the pressure sensor is or comprises a differential pressure sensor.

the pressure sensor is electrically connected to the control unit.

the valve device comprises a proportional valve.

the pressure sensor is configured to supply the control unit with one or more gas pressure measurements ($P_{mask}$), preferably several successive pressure measurements, in the form of numerical values or signals representing such numerical values (for example, voltage signals), which values or signals can be processed as they are or converted into numerical values by the control unit.

the pressure sensor is pneumatically connected, via a pneumatic connection, such as a flexible duct, to a breathing mask in order to take pressure measurements in the internal respiratory chamber of the body of the respiratory interface, e.g. a face mask.

it comprises an electrical power source of the cord and mains plug type (e.g. 110/220 V) and/or an internal battery, preferably rechargeable.

the electrical power source supplies electrical current to the control unit and all of the other components of the apparatus present (depending on the embodiment selected) that require electrical power to operate, for example one or more components such as a display screen, LED, acoustic and/or visual alarm device, etc.

it comprises a rigid external casing, for example made from a polymer or other material.

the control unit, at least part of the internal gas passage, the deformable reservoir, the pressure sensor and/or the valve device are arranged in the casing.

the deformable reservoir comprises a flexible balloon or similar.

the deformable reservoir deforms as a function of the quantity and/or the pressure of therapeutic gas that it contains. It can therefore adopt different states, stages or levels of filling, in particular a so-called "full" stage, a so-called "empty" stage (i.e. minimal residual quantity of gas) and intermediate stages corresponding to partial filling of the reservoir (i.e. between the "full" and "empty" stages).

the pressure sensor is configured or controlled in order to perform pressure measurements ($P_{mask}$) at given time intervals, preferably every 20 msec or less, preferably every 10 msec or less, or even every 5 msec or less.

the control unit is configured to control the valve device, in particular the proportional valve, in order to adjust (i.e. set or modify) the flow rate of gas passing through said valve device as a function of the comparison made by the control unit between the pressure ($P_{mask}$) measured at the respiratory interface, that is to say at the mask, and the predetermined given pressure threshold value ($P_{threshold}$) serving as reference pressure, in particular in order to increase the flow rate of therapeutic gas passing through the valve device and feeding the deformable reservoir, when the control unit determines that the gas pressure ($P_{mask}$) measured in the mask is less than or equal to the given pressure threshold value ($P_{threshold}$), i.e. $P_{mask} \leq P_{threshold}$, where $P_{threshold} \leq 0$ mbar, preferably $P_{threshold} \leq -0.25$ mbar, so as to accelerate the filling of said deformable reservoir.

the deformable reservoir is made from a flexible material of the rubber or silicone type or similar, for example a NuSil LSR silicone rubber.

the control unit with microprocessor comprises one or more microprocessors, preferably one (or more) microcontroller(s).

the one (or more) microprocessor(s) use(s) one or more algorithms.

the control unit comprises one or more data storage memories or similar, for example reference tables.

the control unit with microprocessor comprises an electronic board holding the one or more microprocessors, preferably one or more microcontrollers.

the flow meter or flow rate sensor is arranged in the internal gas passage in order to measure the flow rate of gas circulating in said internal gas passage.

the flow rate sensor (i.e. flow meter) is arranged in the internal gas passage, downstream of the valve device, in particular the proportional valve, so as to be able to measure the flow rate of gas supplied by said valve device.

the flow rate sensor is arranged upstream of the deformable reservoir, preferably upstream of the connection point of the air inlet line.

the flow rate sensor is electrically connected to the control unit and supplies the latter with the measurements that it performs.

the flow rate sensor is or comprises a mass flow sensor or a differential pressure sensor.

it comprises a non-return device arranged in the internal gas passage, downstream of the reservoir, preferably a non-return valve.

the deformable reservoir has a volume of between about 0.1 and 3 L, measured at rest (i.e. internal pressure equal to atmospheric pressure).

the deformable reservoir has a wall with a thickness of between 0.10 and 0.90 mm, typically between 0.25 and 0.75 mm.

the apparatus further comprises one (or more) one-way valve(s) arranged in the internal gas passage, in particular downstream of the deformable reservoir.

the apparatus further comprises a human-machine interface (HMI) comprising an information display screen, preferably a touch screen, and/or one or more selection keys or buttons, particularly virtual keys that are displayed on the touch screen, and/or a starting device, such as an on/off button, and/or other elements.

the alarm means or alarm system are additionally configured to alert the user in the event of a problem affecting the apparatus or the gas, for example a valve or sensor fault, an incorrect gaseous composition (e.g. hypoxic mixture) or other problem.

the alarm means or alarm system can comprise means or a device for emitting acoustic and/or visual signals.

the respiratory interface is a breathing mask.

the breathing mask is a face mask covering the patient's nose and mouth, in use, that is to say when it is worn by said patient.

the respiratory interface, typically a mask, comprises a flexible pad coming into contact with the patient's face and positioning itself on the nose and/or mouth of the patient.

the respiratory interface is a breathing mask comprising a flexible pad carried by a rigid mask body.

the respiratory interface is a breathing mask comprising one or more straps for securing it on the patient's head, typically a harness or similar.

the source of therapeutic gas comprises one or more gas containers, in particularly cylinders.

the source of therapeutic gas comprises a gas container containing an $O_2/N_2O$ gas mixture, preferably an equimolar $O_2/N_2O$ mixture (i.e. 50 mol %/50 mol %).

alternatively, the source of therapeutic gas comprises a gas container containing the binary gaseous mixture $O_2$/argon.

alternatively, the source of therapeutic gas comprises a first gas container containing argon or $N_2O$, a second gas container containing oxygen ($O_2$) and a gas mixer fed with gas by said first and second gas containers, said mixer performing the mixing of the gases coming from the first and second gas containers in order to obtain an $O_2/N_2O$ or $O_2$/argon gas mixture.

it comprises a pressure supply duct. i.e. a pneumatic connection, arranged between the breathing mask and the pressure sensor of the gas delivery apparatus.

BRIEF DESCRIPTION OF THE DRAWINGS

The invention will now be better understood from the following detailed description, which is given by way of a non-limiting illustration, with reference to the appended figures, in which.

DETAILED DESCRIPTION OF PREFERRED EMBODIMENTS

Figure 1:
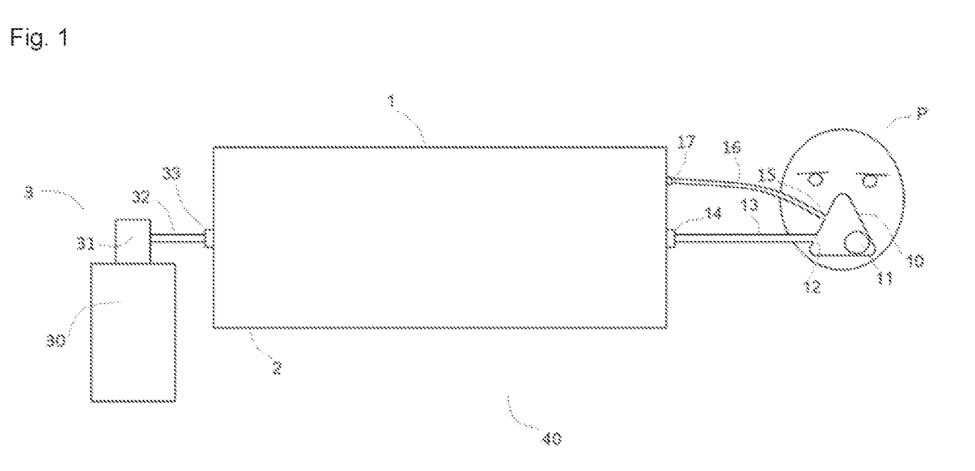
FIG. 1 schematically shows an embodiment of an installation according to the invention for supplying therapeutic gas, FIG. 2 schematically shows an embodiment of the internal architecture of the gas delivery apparatus of the gas supply installation of FIG. 1.

FIG. 1 is a schematic representation of an embodiment of an installation 1 according to the present invention for supplying therapeutic gas.

It comprises a gas delivery apparatus 1, shown in detail in FIG. 2, comprising an external casing 2 forming a rigid shell, for example made from a polymer, comprising the internal components, particularly an internal gas passage, a deformable reservoir, a valve device and a control unit with microprocessor as explained below.

A source 3 of therapeutic gas, such as a gas cylinder 30 provided with a valve 31, supplies a therapeutic gas, that is to say a gas or gas mixture, to the gas delivery apparatus 1 via a connecting hose 32, which is connected to the inlet port 33 of the gas delivery apparatus 1.

The therapeutic gas comprises (at least) a therapeutically effective/active compound, i.e. an active ingredient, having a given initial concentration ($C_{ini}$). For example, the therapeutic gas can be a binary mixture of argon and oxygen ($Ar/O_2$) containing 60% of argon (% by volume) and the remainder of oxygen, in which the argon is the therapeutically effective/active compound.

The therapeutic gas passes through the gas delivery apparatus 1, as explained below, in order then to be delivered to a patient P by means of a gas duct 13 that is fluidly connected to an outlet port 14 of the gas delivery apparatus 1. The gas is supplied to the patient P via a breathing mask 10 fed by the gas duct 13, also called a tube, such as a flexible hose, which gas duct 13 is generally several metres long, typically about 3 or 4 metres long, or even longer in some cases.

Preferably, the breathing mask 10 is a face mask, i.e. a mask covering the patient's mouth and nose. Other similar or equivalent respiratory interfaces could of course be suitable.

The mask 10, here a face mask, has an exhalation port 11, also called vent, communicating fluidically with the ambient atmosphere, and an inhalation port 12 which is connected fluidically to the gas duct 13 through which the gas is conveyed. The exhalation port 11 preferably comprises a non-return valve which directs and permits the discharge of the gases to the atmosphere when the patient exhales, that is to say exhaled gases rich in $CO_2$, and also prevents ambient air from entering the mask 10 when the patient inhales the therapeutic gas, that is to say during their inspiratory phases. The non-return valve comprises a one-way valve, such as a silicone disc resting on a perforated surface, which only allows the gas to pass through in one direction, for example the one-way valve with part reference 97351 sold by Qosina.

The mask 10 furthermore has a pressure tapping port 15 fluidically connected to a pressure supply line or duct 16, such as flexible tube, for example a silicone tube several metres long, in turn pneumatically connected to the pressure sensor 55, via a measuring port 17 arranged on the casing 2 of the gas delivery apparatus 1. This configuration allows the pressure sensor 55 arranged in the casing 2 to take pressure measurements in the mask 10 in order to monitor the pressure (i.e. vacuum) prevailing therein, as explained below.

The gas source 3 contains the therapeutic gas under pressure, typically at a maximum pressure of the order of 250 bar, or even higher. The valve 31 is preferably an integrated pressure regulator valve delivering the gas to the connecting hose 32 at a reduced pressure of below 10 bar, for example of the order of 3 to 5 bar. The integrated pressure regulator 31 is preferably protected by a rigid cap (not shown).

Figure 2:
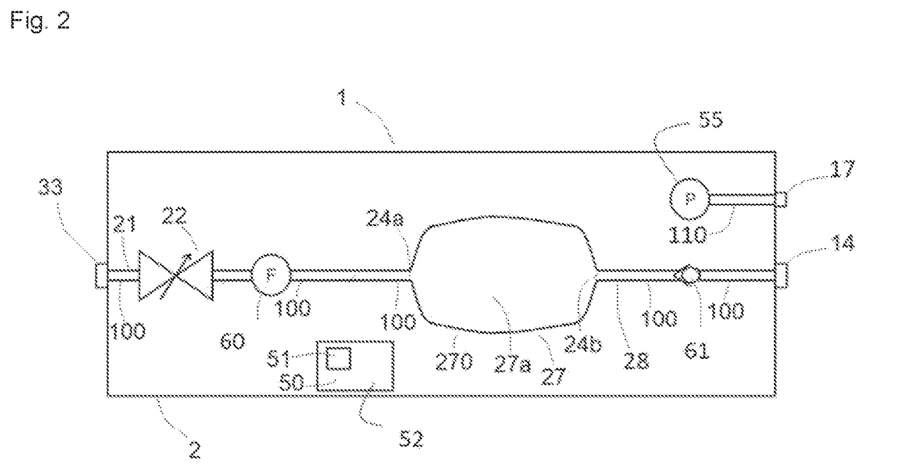

FIG. 2 schematically shows an embodiment of the internal architecture of the gas delivery apparatus 1 of the gas supply installation 40 according to the present invention, which is schematically shown in FIG. 1.

The gas delivery apparatus 1 comprises a control unit 50 comprising a microprocessor 51 held by an electronic board 52 serving in particular to control a valve device 22, such as a proportional valve, in order to set or adjust the flow rate of gas passing through said valve device 22.

The control unit 50 comprises one or more microprocessors 51 typically one or more microcontrollers, executing one or more algorithms, that receive and analyse the measurements supplied by various sensors, in particular by the pressure sensor 55 arranged in the casing 2 and pneumatically connected to the mask 10 by the pressure supply line 16. The control unit 50 also performs calculations, comparisons or other tasks as are explained below.

An internal gas passage 100, for example a duct or similar, is arranged in the casing 2 and extends between an inlet port or orifice 33 and an outlet port or orifice 14 so as to convey the therapeutic gas from the inlet port 33 to the outlet port 14 and then allow it to be conveyed to the mask 10, via the flexible duct 13.

The valve device 22, namely a proportional valve here, is arranged in the internal gas passage 100, preferably in the upstream section 21 of said internal gas passage 100. It is controlled by the microcontroller 51 of the control unit 50 in order to modify the flow rate of therapeutic gas passing through said valve device 22 and circulating in the lumen of the internal gas passage 100 towards the outlet port or orifice 14, as described below.

Various types of proportional valves can be used as a valve device 22; preferably, a proportional valve that operates over a wide range of flow rates is selected, for example the valve designated as IMI FAS FLATPROP.

A flow rate sensor 60 is arranged in the internal gas passage 100, at the outlet of the valve device 22, in order to measure the flow rate of the therapeutic gas delivered by the valve device 22, typically a proportional valve. The flow rate sensor 60 can be a mass flow sensor or can be based on a differential pressure sensor.

The flow rate sensor 60 is electrically connected to the control unit 50 and delivers a flow rate signal that is processed by said control unit 50, typically by the microprocessor 51, preferably a microcontroller.

Preferably, a volumetric flow rate is obtained after conversion of the signal supplied by the flow rate sensor 60 using one or more specific look-up tables stored in a memory interacting with the control unit 50. The flow rate sensor 60 can also be used to detect any faults of the proportional valve 22 or to determine the quantity of gas, that is to say the volume, delivered by the gas source 3.

The internal gas passage 100 then conveys the gas to a deformable reservoir 27, in particular a flexible reservoir, positioned downstream of the flow rate sensor 60, and fluidically connected to said gas passage 100.

The deformable reservoir 27 comprises a flexible peripheral wall 270 defining an internal volume 27a for the gas, forming a deformable pouch for the therapeutic gas. At rest, the internal volume 27a is for example between approximately 0.2 and 1 L.

The gas flow enters the internal volume 27a of the deformable reservoir 27 through a reservoir inlet orifice 24a, in fluidic communication with the internal gas passage 100. Preferably, the properties of the deformable reservoir 27 are such that it is highly deformable. For example, its peripheral wall 270 has a thickness of between approximately 0.25 and 0.75 mm and is made from a biocompatible flexible silicone, for example silicone from the LSR range sold by NuSil.

The gas leaves the reservoir 27 through a reservoir outlet orifice 24b that is fluidically connected to a downstream section 28 of the internal gas passage 100, extending as far as the outlet port 14.

One or more non-return devices 61, such as a non-return valve, are positioned in the internal gas passage 100, downstream of the reservoir 27, namely between the outlet orifice 24b of the reservoir 27 and the outlet port 14 of the casing 2, in order to prevent any backflow of gas. The gases exhaled by the patient P are thus discharged solely through the exhalation port 11 of the mask 10 and cannot return to the reservoir 27.

The non-return valve 61 is preferably designed such that a very small drop in pressure, typically less than or equal to 0.2 mbar, is generated across it, when a gas flow passes through it.

Of course, several non-return valves 61 can be used instead of just one, for example 3 to 5 of them positioned in parallel (not shown).

In order to make it possible to take pressure measurements in the mask 10, a pressure sensor 55, preferably a differential pressure sensor, is provided in the casing 2 of the apparatus 1. The pressure sensor 55 is configured to measure both negative pressures (that is to say pressures below atmospheric pressure or vacuums) to about −5 mb and positive pressures (that is to say pressures above atmospheric pressure or overpressures) to about +5 mb.

Here, the pressure sensor 55 is a differential pressure sensor that comprises two detection orifices comprising a first detection orifice kept in atmospheric conditions (that is, at atmospheric pressure, i.e. 1 atm) and a second detection orifice positioned in a measuring duct 110, connected to the measuring port 17 of the casing 2. The measuring port 17 is fluidically connected to the pressure supply line 16 connected to the mask 10 in order to monitor the pressure prevailing in the respiratory chamber of said mask 10. For example, the differential pressure sensor with part reference SPD3X available from Sensirion can be used.

At successive time intervals, for example at a frequency of 5 msec, the differential pressure sensor 55 sends a pressure measurement signal $P_{mask}$ to the control unit 50, which signal $P_{mask}$ reflects the pressure measured in the mask 10 at the time in question. The control unit 50 then processes this pressure signal in order to control the proportional valve 22, in order to adjust the flow rate of gas sent to the flexible reservoir 27.

The flexible reservoir 27 has various inflation/deflation states as a function of the gas pressure prevailing therein, and therefore as a function of the quantity of gas that is introduced into it or withdrawn from it, comprising at least:
- a so-called "rest" state, in which the internal volume 27a, filled with gas, is at atmospheric pressure (i.e. 1 atm).
- a so-called "inflated" state, in which the internal volume 27a, filled with gas, is at a pressure higher than ambient pressure (that is, >1 atm).
- "partially deflated" states, in which some of the gas contained in the reservoir has left it.

A power source (not shown) supplies electrical current to all of the components that operate using electrical energy, such as sensors, control unit, controlled valves, human-machine interface (HMI), digital display screen, etc. It can be positioned in the casing 2, for example a rechargeable battery, or comprises a cord and a mains plug (110/220 V), and optionally a current converter.

During therapy with administration of therapeutic gas, the patient P performs a succession of inspirations and exhalations in order to inhale the therapeutic gas, for example an $O_2$/argon or $N_2O/O_2$ mixture, and exhale the $CO_2$-rich gases resulting from the pulmonary exchanges.

In order to facilitate understanding of how the apparatus 1 operates, it is considered that:
- the pressure in the internal volume 27a of the reservoir 27 is equal to atmospheric pressure, that is to say the reservoir 27 is in the rest position.
- the reservoir 27 is filled with the therapeutic gas coming from the gas source 3.
- the patient is initiating an inhalation.

When the patient starts to inhale, the exhalation port 11 of the mask 10 is closed and a slight vacuum occurs at the inhalation port 12 of the mask. This vacuum spreads to the differential pressure sensor 55, respectively via the pressure supply line 16, the measuring port 17 and the measuring duct 110. The pressure information is then transmitted by the differential pressure sensor 55 to the processing unit 50, in particular to the microprocessor 51.

In addition, this vacuum spreads in parallel in the duct 13, the outlet port 14 and the downstream section 28 of the internal gas passage 100.

When the gas pressure in the internal volume 27a of the reservoir 27 is equal to atmospheric pressure (i.e. 1 atm), a positive differential pressure then occurs through the non-return valve 61, which allows a certain quantity of gas to pass through said non-return valve 61, in order to meet the patient's respiratory demand.

In other words, a flow rate of gas can be established from the reservoir 27 towards the mask 10. As a result, the internal volume 27a of the reservoir 27 then empties and the reservoir 27 deflates, in turn creating a slight vacuum in the internal volume 27a.

The control unit 50 is configured to ensure that at any time the pressure prevailing in the mask 10 is as close as possible to atmospheric pressure (i.e. 1 atm), i.e. 0 mbar relative. To do this, the control unit 50 controls the proportional valve 22 so that the flow rate supplied by said proportional valve 22 is proportional to the pressure $P_{mask}$ measured in the mask 10 by the differential pressure sensor 55.

To this end, the microprocessor 51 can for example implement an algorithm of the following type:

If "Mask pressure" is negative: Flow rate (IL/min)=$\alpha$*|P|

If "Mask pressure" is positive: Flow rate (L/min)=0 where: $\alpha$ is a positive constant and |P| is the absolute value of the pressure measured in the mask.

The control unit 50 therefore only acts on the proportional valve 22 if the pressure prevailing in the mask 10 is negative, that is to say the proportional valve 22 is controlled to or stays in the closed position as soon as the pressure in the mask 10 becomes positive.

If the case of negative pressure (i.e. vacuum) in the mask 10, measured by the differential pressure sensor 55, reflecting inhalation by the patient P, the proportional valve 22 will be controlled by the control unit 50, in particular by the microprocessor 51, such that: Flow rate (L/min)=α*|P|.

A proportionality then occurs between the flow rate delivered by the proportional valve 22 and the negative pressure measured in the mask 10 by the differential pressure sensor 55. The further away the pressure value moves from 0 mb, the higher the flow rate. Conversely, the closer the pressure value moves to 0 mb, the lower the flow rate. It will of course be understood that the algorithm described here is for illustration, and that more sophisticated algorithms such as control by proportional, integral and derivative terms (PID) could be implemented.

Furthermore, the gas delivery apparatus 1 can comprise other elements, such as a human-machine interface (HMI) with information display screen, preferably a touch screen, one or more selection keys or buttons, a starting device, such as an on/off button, an alarm system and/or other elements.

In such an installation 40 for supplying therapeutic gas, it has been found in practice that leaks, i.e. losses of leaktightness, could appear at the level of the respiratory mask 10, in particular at the perimeter of the mask 10, that is to say the zone of contact with the patient's face, which zone can comprise a flexible pad.

This undesirable admission of ambient air is all the greater the longer the gas supply line 13. In fact, this gas supply line 13 induces a resistance to inhalation that increases with its length and then requires the patient to produce a negative pressure (i.e. a vacuum) so as to be able to inhale the quantity of gas needed as the resistance of the line 13 increases.

Consequently, in the case of "leaks" at the level of the mask, that is to say losses of leaktightness, this negative pressure entrains ambient air which then enters the mask and dilutes the therapeutic gas, during the inspiratory phases of the patient, which is problematic since it may lead to considerably lowered efficacy of the active compound contained in the therapeutic gas administered to the patient. Thus, certain therapeutic properties of argon diminish once its concentration is less than 50% by volume.

To solve this problem, the installation 40 of the invention is configured to verify that the undesired dilution of the therapeutic gas is not excessive, that is to say not sufficient to negatively impact the efficacy of treatment of the patient, and, if appropriate, to warn the user of excessive dilution, that is to say an insufficient concentration of active compound in the gas supplied to the patient P.

More precisely, to do this, storage means are provided for storing a concentration threshold value ($C_{min}$) of therapeutically active compound, for example a flash memory arranged in the apparatus.

Figure 3:
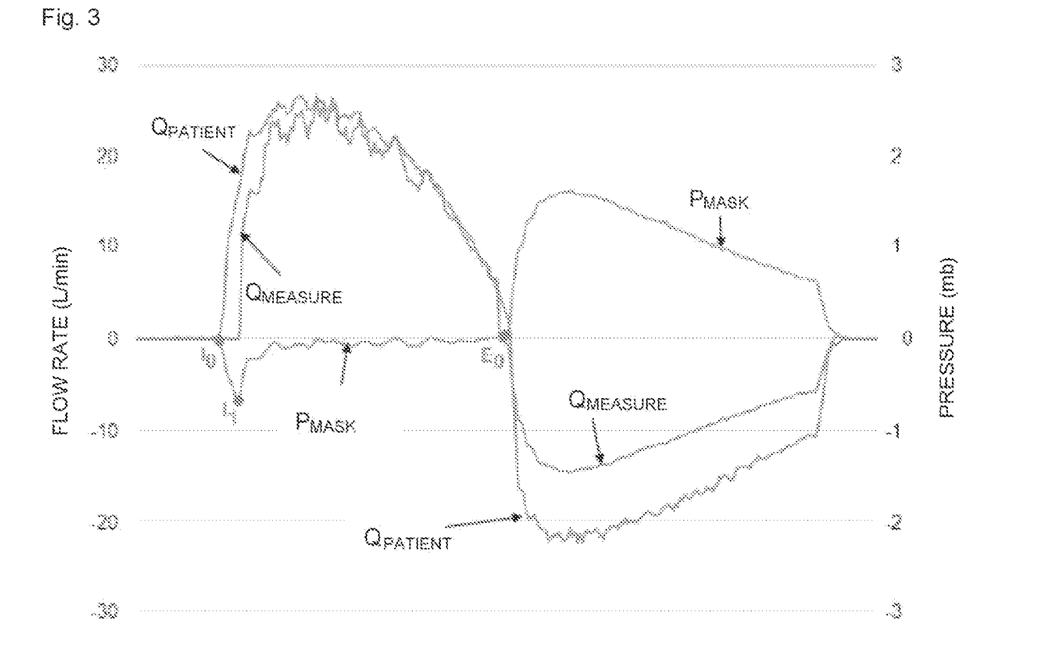
FIG. 3 shows flow rate and pressure curves obtained during a respiratory cycle of the patient.

Furthermore, the control unit 50 is configured to be able to estimate the leaks at the level of the respiratory mask 10 during the respiratory cycles of the patient, that is to say the losses of leaktightness leading to the admission of ambient air susceptible of diluting the therapeutic gas, this so as to be able to warn the user in the event of excessive dilution of the active compound of said therapeutic gas. As is illustrated in FIG. 3 and explained below, each respiratory cycle comprises a inspiratory phase or period (I), during which the patient inspires/inhales gas, which is followed by an expiratory phase or period E, during which the patient expires/exhales gas enriched in $CO_2$.

More precisely, the control unit 50 first determines the exhaled flow rate ($Q_{exp}$) escaping through the exhalation port 11 of the mask 10, in particular a face mask, on the basis of the gas pressure ($P_{mask}$) measured at said mask 10, during an/each expiratory phase of the patient P, that is to say when the patient exhales gases charged with $CO_2$, which are evacuated to the atmosphere via the exhalation port 11 of the mask 10.

It then determines, on the basis of the flow rate of gas supplied ($Q_{alim}$) during an (each) inspiratory phase of the patient and on the basis of the exhaled flow rate ($Q_{exp}$) during the expiratory phase following this inspiratory phase, volumes of gas supplied ($V_{alim}$) and exhaled ($V_{exp}$), and determines, on the basis of these volumes of gas supplied ($V_{alim}$) and exhaled ($V_{exp}$), and on the basis of the integral of the gas pressure ($P_{mask}$) during the inspiratory phase and the integral of the gas pressure ($P_{mask}$) during the expiratory phase, at least one leakage volume ($V_{leak}$) which enters the mask 10 during said inspiratory phase. The integrals are calculated by the microprocessor of the control unit 50.

The leakage volume ($V_{leak}$) and the volumes of gas supplied ($V_{alim}$) and exhaled ($V_{exp}$) then allow the control unit 50 to calculate a rate of dilution of the gas, for example expressed as a percentage (D %).

Since the rate of dilution of the gas has been determined and the initial concentration ($C_{ini}$) of the therapeutically active compound contained in the therapeutic gas, for example of the argon contained in a $Ar/O_2$ mixture, is also known, the control unit 50 is able to calculate the actual concentration ($C_{actual}$) of the therapeutically active compound within the mask 10, that is to say the concentration actually supplied to the patient P, which depends on the leakage at the mask, that is to say undesirable admission of air resulting from the loss of leaktightness.

The initial concentration ($C_{ini}$) of the therapeutically active compound contained in the therapeutic gas is known and is preferably stored by the control unit 50, in particular by the microprocessor. This initial concentration ($C_{ini}$) can be indicated, adjusted or changed by the user via a human-machine interface or HMI. The HMI can also serve to specify the type of therapeutic gas, i.e. the nature and composition of a gaseous mixture.

By comparing the calculated actual concentration ($C_{actual}$) to the concentration threshold value ($C_{min}$) stored by the storage means, the control unit 50 is able to determine if the calculated actual concentration ($C_{actual}$) is or is not below the concentration threshold value ($C_{min}$) and, if appropriate, order the alarm means to trigger an acoustic and/or visual alarm in order to warn the user of an excessive dilution resulting from considerable leakage (i.e. loss of leaktightness) at the mask 10.

The user is then able to check the positioning of the mask 10 on the patient's face and, if necessary, adjust it so as to minimize or eliminate the loss of leaktightness, i.e. the leakage.

FIG. 3 proposes flow rate and pressure curves over time, illustrating diagrammatically the functioning of the control unit 50 of the installation 40 of the invention, in particular of the algorithm(s) used by the microprocessor 51 of the control unit 50 of the gas delivery apparatus 1, during a respiratory cycle, that is to say during the inspiratory (I) and expiratory (E) phases of the patient P, in order to make it possible to determine the impact of the leakage, that is to say evaluate/estimate the level (i.e. rate) of dilution of the therapeutic gas by ambient air.

These curves have been obtained on a test bench comprising an "electronic patient", namely a device simulating a patient's breathing, for example the breathing simulator ASL 5000 available from Ingmar Medical.

The gas delivery apparatus 1 is connected to the "electronic patient" by means of a gas-conveying duct with a calibrated orifice or orifices simulating one or more leaks at the level of the breathing mask 10.

More precisely, FIG. 3 shows a respiratory cycle of a patient P where:

$Q_{PATIENT}$ is the flow rate of gas respectively inhaled and exhaled by the patient at the level of the trachea. This flow rate cannot be known by the gas delivery apparatus 1.

$P_{MASK}$ is the pressure measured in the breathing mask 10 by the gas delivery apparatus 1.

$Q_{MEASURE}$ is the flow rate measured by the gas delivery apparatus 1 during the respiratory cycle of the patient P.

The inhalation by the patient P is split into two successive distinct phases $I_0$, $I_1$ where $I_0$ corresponds to the very start of inhalation. This inhalation flow rate can be detected once the pressure $P_{MASK}$ passes below a predetermined threshold recorded in the control unit 50, for example a strictly negative value. At this moment, the relative pressure in the reservoir 27 is zero, that is to say atmospheric pressure (i.e. 1 atm).

As has been mentioned above, the inhalation by the patient then creates a vacuum in the mask 10. In response to this vacuum, the control unit 50 will control the proportional valve 22 to adjust the therapeutic gas flow in order to limit the pressure drop in the mask 10.

As in any system incorporating electromechanical elements, there is an intrinsic response time, that is to say a delay, in response to the physical manifestation, which here is the vacuum in the mask 10.

During this phase $I_0$, the pressure in the mask 10 decreases, which causes:

a decrease of the pressure in the deformable reservoir 27, a sign that the latter is deflating and that a quantity of gas, i.e. a flow rate, is passing through the non-return valve 61 in the direction of the breathing mask 10.

entrainment of ambient air into the mask 10, via the leaks present at the perimeter of the breathing mask 10, which contributes to the dilution of the therapeutic gas supplied by the gas delivery apparatus 1 and inhaled by the patient P.

This drop in pressure in the breathing mask 10 reaches, at $I_1$, a minimum value, which corresponds to the moment when the proportional solenoid valve 22 begins to open in response to the request of the control unit 50 and thus to deliver a gas flow rate in order to meet the need of the patient P, thereby increasing the pressure in the breathing mask 10 and keeping it as close as possible to 0.

The elements upstream of the breathing mask 10, that is to say mainly the line 13, but also the non-return valve 61 and the downstream section 28 of the passage 100 (as far as the outlet orifice 24b of the reservoir 27), create a resistance to the flow of the gas.

In relation to the inspiratory demand of the patient P, that is to say their inspiratory flow rate, this resistance to the flow is equal to the difference between the pressure in the reservoir 27 and the pressure in the mask 10. Thus, when the pressure in the breathing mask 10 approaches 0, while the gas delivery apparatus 1 supplies a flow rate of gas to the patient P, the pressure prevailing in the reservoir 27 is positive.

If the apparatus 1 did not have a flow rate delivery mechanism based on the pressure prevailing in the mask 10, that is to say if the reservoir 27 emptied progressively in response to the inhalation by the patient P, then the vacuum in the mask 10 allowing the patient P to meet their respiratory needs would be equal to the sum of the flow resistances of the elements situated downstream of the reservoir 27, including the reservoir 27 itself. This would then require the patient to exert considerable inhalation effort, causing discomfort, and would impose greater negative pressure in the breathing mask 10, thus accentuating the admission of ambient air through the leaks around said breathing mask 10 and thereby reducing the concentration of therapeutic gas inhaled by the patient.

The inhalation by the patient P then gives way to an expiratory phase $E_0$, in which the patient exhales through the exhalation port 11 of the mask 10. This exhalation then generates a positive pressure in the mask 10, and the control unit 50 then controls the proportional valve 22 so as to interrupt the delivery of gas, that is to say the flow rate.

In a manner analogous to the detection of the inhalation $I_0$, the determination of the change-over to exhalation can be considered to take place when the pressure $P_{MASK}$ passes above a predetermined and recorded threshold in the control unit 50, for example a strictly positive value.

The exhalation port 11 of the mask 10 provides a resistance to the flow, i.e. to a flow rate. Given that this exhalation port 11 opens out to ambient air, that is to say to atmospheric pressure, there is a relationship between the pressure $P_{MASK}$ measured in the breathing mask 10 and the flow rate circulating in said exhalation port 11. Thus, with a conversion table having been registered beforehand in the control unit 50, the microprocessor 51 is able to determine the flow rate $Q_{MEASURE}$ escaping through the exhalation port 11, by real-time analysis of the pressure $P_{MASK}$ prevailing in the breathing mask 10.

The following sequence aims to demonstrate the capacity of the respiratory gas delivery apparatus 1 to determine the concentration of therapeutic gas inhaled by the patient P and to ensure that this is greater than a given minimum value that has been pre-recorded, i.e. stored, namely a minimum concentration of active compound in the therapeutic gas, and this despite the dilution caused by the admission of air due to the abovementioned loss of leaktightness.

To put it another way, the respiratory gas delivery apparatus 1 of the installation 40 of the invention makes it possible to ensure that the dilution is not excessive, and it does so in the following way.

During the phase $I_0$-$E_0$ corresponding to the inhalation by the patient P, the following equation may be considered:

$$Q_{PATIENT} = Q_{MESURE} + Q_{FUITE}$$

where:

$Q_{PATIENT}$ is the flow rate inhaled by the patient, $Q_{MEASURE}$ is the flow rate delivered by the proportional solenoid valve 22 and measured by the flow rate sensor 60, $Q_{LEAK}$ is the flow rate introduced by the leaks (due to the losses of leaktightness) at the perimeter of the breathing mask 10 during this inspiratory phase.

Now, the leakage flow rate $Q_{LEAK}$ can also be seen as an element allowing a gas to circulate, hence having a resistance to the flow. Since the ambient pressure prevails outside the breathing mask 10, it may be considered that the flow rate introduced by the leakage $Q_{LEAK}$ is such that:

$$Q_{FUITE} = -\beta \cdot P_{MASQUE}$$

where:

$\beta$ is an unknown constant, $P_{MASK}$ is the pressure prevailing in the breathing mask 10. When $P_{MASK}$ is negative, $Q_{LEAK}$ is positive.

Hence: $Q_{PATIENT} = Q_{MESURE} - \beta \cdot P_{MASQUE}$

By calculating the integral of these variables, during the inhalation by the patient P, that is to say on the interval [$I_0$, $E_0$], this gives $$V_{PATIENT1} = V_{MESURE1} - \beta \int_{I0}^{E0} P_{MASQUE}$$

where:
- $V_{PATIENT1}$ is the volume inhaled by the patient during the inspiratory phase,
- $V_{MESURE1}$ is the volume delivered by the gas delivery apparatus 1, calculated by the microprocessor 51 in response to the data supplied by the flow rate sensor 60.

Analogously, the exhalation by the patient P on the interval $E_0$-$I_0$ (considering $I_0$ the detection of the inhalation succeeding this exhalation) gives:

$$Q_{PATIENT} = Q_{MESURE} + Q_{FUITE}$$

where:
- $Q_{PATIENT}$ is the flow rate exhaled by the patient,
- $Q_{MESURE}$ is the flow rate measured by the microprocessor 51 according to the curve recorded in the control unit 50, correlating the pressure $P_{MASK}$ prevailing in the breathing mask 10 and the flow rate passing through the exhalation port 11.
- $Q_{LEAK}$ is the flow rate escaping from the leaks of the breathing mask 10 during the inspiratory phase, on account of the positive nature of the pressure $P_{MASK}$.

Considering that the constant $\beta$ remains identical between the inspiratory and expiratory phases, that is to say that the positioning of the mask 10 does not change, a similar reasoning gives the following:

$$V_{PATIENT\ E} = V_{MESURE\ E} + \beta \int_{E0}^{I0} P_{MASQUE}$$

Now, the volume inhaled by a patient P is generally equivalent to the exhaled volume, hence:

$$V_{MESURE\ I} - \beta \int_{I0}^{E0} P_{MASQUE} = V_{MESURE\ E} + \beta \int_{E0}^{I0} P_{MASQUE}$$

And so $\beta$ can be calculated in the form:

$$\beta = \frac{V_{MESURE\ I} - V_{MESURE\ E}}{\int_{E0}^{I0} P_{MASQUE} + \int_{I0}^{E0} P_{MASQUE}}$$

Hence, if: $V_{PATIENT\ I} = V_{MESURE\ I} - \beta \int_{I0}^{E0} P_{MASQUE}$ it is then possible to determine the rate (D %) of dilution, in terms of the volume that the patient has inhaled with respect to the volume that the gas delivery apparatus 1 has supplied, i.e. the rate of dilution given by the following equation:

$$D\% = \frac{V_{MESURE\ I}}{V_{MESURE\ I} - \beta \int_{I0}^{E0} P_{MASQUE}}$$

D % is expressed here in percentage.

For example, the microprocessor 51 is capable of determining that the volume of gas $V_{MESURE\ I}$ supplied by the delivery apparatus 1 during inhalation is of the order of 440 mL, while the volume exhaled $V_{MESURE\ E}$, that is to say the volume of gas escaping through the exhalation port 11 of the mask, is of the order of 300 mL, which could mean that the leakage at the perimeter of the mask 10 is quite considerable, since the difference between these two volumes is of the order of 140 mL.

Furthermore, the pressure in the breathing mask 10 during the inspiratory phase is negative, that is to say a supplementary volume will be introduced by this leak during said inspiratory phase. In the same way, on account of the positive pressure in the breathing mask 10 during the expiratory phase, some of the volume exhaled by the patient P will escape to the atmosphere via this same leak.

Now, given that the pressure in the breathing mask 10 remains very close to 0 during the inspiratory phase, the addition of the leakage volume during the inspiratory phase is relatively small, in respect of the volume escaping via this same leak during the expiratory phase, since the pressure in the breathing mask 10 is then much more pronounced, i.e. much higher. By analysing the development of the flow rate and pressure during the respiratory cycle (i.e. inhalation and exhalation) and according to the equation set out above, the microprocessor 51 is able to determine that the volume introduced by this leak during the inspiratory phase is limited to just 20 mL, and can thus calculate the percentage dilution D % (calculated by volume), i.e. about 96.3% of the initial concentration ($C_{ini}$) of active compound of the therapeutic gas.

Thus, taking the example of an $Ar/O_2$ mixture containing an initial concentration ($C_{ini}$) of argon equal to about 60 vol. % coming from the gas source 3, the actual concentration of argon (active compound) in the therapeutic gas, determined by the microprocessor 51, is then of the order of 57 vol. %, hence above the 50% threshold value below which argon is no longer effective in some treatments, which guarantees the efficacy of the $Ar/O_2$ mixture despite its dilution by ambient air originating from the leaks.

Generally, by performing such measurements and calculations (quasi) continuously, that is to say preferably for each respiratory cycle of the patient, the gas delivery apparatus 1, especially the control unit 50 with microprocessor 51, is able to determine if the actual concentration ($C_{actual}$) of active compound in the therapeutic gas is or is not above a concentration threshold value ($C_{min}$) of therapeutically active compound, which value is stored by the storage means, for example a flash memory or directly in the microprocessor 51.

When the actual concentration ($C_{actual}$) drops below the stored concentration threshold value ($C_{min}$) of therapeutically active compound, for example below 50 vol. % in the example of argon, the microprocessor 51 is configured to actuate alarm means and thus trigger an acoustic and/or visual alarm intended to warn the user that there is excessive dilution, which is equivalent to considerable leakages that often signify that the mask 10 of the patient P is poorly positioned.

Preferably, the control unit 50 and the microprocessor 51 are able to limit the triggering of false alarms by calculating one or more averages from concentration values obtained over several cycles, and by working on these averages rather than on instantaneous values.

The alarm means allowing the acoustic and/or visual alarm to be triggered comprise, for example, a loudspeaker for issuing an audio signal and/or one or more light-emitting diodes (LED) for supplying a visual signal, for example blinking of the LED, or similar.

Generally speaking, the installation of the invention can be used to perform administration, to a patient, of a therapeutic gas composed of a mixture of several gaseous constituents, for example a mixture of argon and oxygen (60 vol. % Ar/40 vol. % $O_2$), to be inhaled before and during, even after, a mechanical thrombectomy procedure aimed at treating a cerebrovascular accident (CVA) in humans.

What is claimed is:

1. An apparatus (40) for supplying therapeutic gas, comprising:
a source (3) of a gas comprising at least one therapeutically active compound at an initial concentration ($C_{ini}$),
a gas delivery apparatus (1) fed with the gas by said gas source (3), and
a respiratory interface (10) provided with at least one exhalation port (11) which is fed with the gas by said gas delivery apparatus (1), wherein the gas delivery apparatus (1) comprises:
an internal gas passage (100) in fluidic communication with a deformable reservoir (27) configured for and adapted to feed the deformable reservoir (27) with the gas,
a valve (22) arranged on the internal gas passage (100), upstream of the deformable reservoir (27), configured for and adapted to control a flow rate of the gas circulating in the internal gas passage (100) ($Q_{alim}$),
a control unit (50) with a microprocessor (51) which is configured for and adapted to control the valve (22) to thereby control the flow rate of the gas passing through the valve (22) and feed the deformable reservoir (27) with the gas,
a pressure sensor (55) configured for and adapted to perform one or more gas pressure measurements ($P_{mask}$) of a gas pressure at the respiratory interface (10) and to supply said one or more gas pressure measurements ($P_{mask}$) to the control unit (50),
a flow rate sensor (60) arranged in the internal gas passage (100) configured for and adapted to measure the flow rate of supplied gas ($Q_{alim}$) circulating in said internal gas passage (100) and to supply said gas flow rate measurement (Q) to the control unit (50), and
an acoustic and/or visual alarm,
further characterized in that:
the gas delivery apparatus (1) additionally comprises a data storage device for storing a concentration threshold value ($C_{min}$) of the at least one therapeutically active compound, and
the control unit (50) is specifically programmed and thereby configured for and adapted to:
i) determine an exhaled flow rate ($Q_{exp}$) escaping through the exhalation port (11) of the respiratory interface (10) on the basis of the gas pressure ($P_{mask}$) measured at the respiratory interface (10), during at least one expiratory phase of said patient,
ii) determine, on the basis of the flow rate of supplied gas ($Q_{alim}$) during an inspiratory phase of the patient and of the exhaled flow rate ($Q_{exp}$) during the expiratory phase following said inspiratory phase of the patient, a volume of the gas supplied ($V_{alim}$) and a volume of an exhalation gas exhaled ($V_{exp}$),
iii) determine, on the basis of the volumes of gas supplied ($V_{alim}$) and exhaled ($V_{exp}$), from the integral of the gas pressure ($P_{mask}$) during the inspiratory phase and the integral of the gas pressure ($P_{mask}$) during the expiratory phase, at least one leakage volume ($V_{leak}$) entering the respiratory interface (10) during said inspiratory phase,
iv) determine, on the basis of the leakage volume ($V_{leak}$) and the volumes of gas supplied ($V_{alim}$) and exhaled ($V_{exp}$), a rate of dilution of the gas (D %),
v) calculate the actual concentration ($C_{actual}$) of said at least one therapeutically active compound in the respiratory interface (10) on the basis of the initial concentration ($C_{ini}$) of said at least one therapeutically active compound and of the determined rate of dilution of the gas,
vi) compare the calculated actual concentration ($C_{actual}$) to the concentration threshold value ($C_{min}$) of the at least one therapeutically active compound, stored by the data storage device, and
vii) trigger an acoustic and/or visual alarm when the calculated actual concentration ($C_{actual}$) is below said stored concentration threshold value ($C_{min}$) of the at least one therapeutically active compound.

2. The apparatus according to claim 1, characterized in that the respiratory interface (10) is a breathing face mask.

3. The apparatus according to claim 1, characterized in that the control unit (50) of the gas delivery apparatus (1) is configured to determine the exhaled flow rate ($Q_{exp}$) on the basis of (i) the gas pressure ($P_{mask}$) measured at the respiratory interface (10) and (ii) at least one stored conversion table.

4. The apparatus according to claim 1, characterized in that the gas source (3) comprises argon as the at least one therapeutically active compound at an initial concentration ($C_{ini}$) of greater than 50% by volume.

5. The apparatus according to claim 4, characterized in that the concentration threshold value ($C_{min}$) stored is equal to 50% by volume.

6. The apparatus according to claim 1, characterized in that the pressure sensor (55) comprises a differential pressure sensor.

7. The apparatus according to claim 1, characterized in that the pressure sensor (55) is configured or controlled to perform pressure measurements ($P_{mask}$) every 20 msec or less.

8. The apparatus according to claim 1, characterized in that the valve (22) comprises a proportional valve.

9. The apparatus according to claim 1, characterized in that the flow rate sensor (60) is arranged in the internal gas passage, downstream of the valve (22) and upstream of the deformable reservoir (27).

10. The apparatus according to claim 1, characterized in that the flow rate sensor (60) comprises a mass flow rate sensor or a differential pressure sensor.

11. The apparatus according to claim 1, characterized in that the control unit (50) is configured for and adapted to control the valve (22) to increase the flow rate of therapeutic gas passing through said valve device (22) and feeding the deformable reservoir (27), when the control unit (50) determines that the gas pressure ($P_{mask}$) measured in the respiratory interface (10) is less than or equal to ($P_{mask} \leq P_{threshold}$) a given pressure threshold value ($P_{threshold}$).

12. The apparatus according to claim 11, characterized in that the pressure threshold value ($P_{threshold}$) is less than or equal to 0 mbar.

13. The apparatus according to claim 11, characterized in that the pressure threshold value ($P_{threshold}$) is less than or equal to −0.25 mbar.

14. The apparatus according to claim 11, characterized in that the pressure threshold value ($P_{threshold}$) is stored in the control unit (50).

15. The apparatus according to claim 11, characterized in that the pressure threshold value ($P_{threshold}$) is adjustable.

* * * * *